United States Patent [19]

Schneider et al.

[11] Patent Number: 5,614,643
[45] Date of Patent: Mar. 25, 1997

[54] PROCESS FOR THE ENZYMATIC PRODUCTION OF ISOMERICALLY PURE ISOSORBIDE-2 AND 5-MONOESTERS AS WELL AS THEIR CONVERSION INTO ISOSORBIDE-2- AND 5-NITRATE

[75] Inventors: Manfred Schneider; Robert Seemayer, both of Wuppertal, Germany

[73] Assignee: Boehringer Mannheim GmbH, Mannheim, Germany

[21] Appl. No.: 481,915

[22] Filed: Jun. 7, 1995

Related U.S. Application Data

[60] Division of Ser. No. 191,731, Feb. 4, 1994, Pat. No. 5,538,891, which is a continuation-in-part of Ser. No. 938,938, Sep. 1, 1992, abandoned.

[30] Foreign Application Priority Data

Sep. 2, 1991 [DE] Germany .................. 41 29 093.3

[51] Int. Cl.$^6$ .................................................. C07D 493/00
[52] U.S. Cl. .................................................. 549/464
[58] Field of Search ................................ 549/465, 464

[56] References Cited

U.S. PATENT DOCUMENTS 5,538,891   7/1996   Schneider et al. .................. 435/280

*Primary Examiner*—Amelia A. Owens
*Attorney, Agent, or Firm*—Felfe & Lynch

[57] ABSTRACT

Process for the enzymatic production of isomerically pure compounds having the general formulae I and II

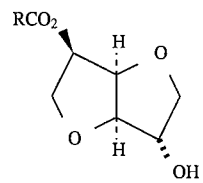

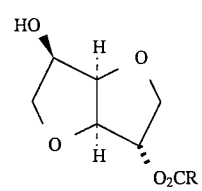

in which the substituents R have the meanings stated in the claims, as well as their use for the production of isomerically pure isosorbide-2-nitrate having the formula V and isosorbide-5-nitrate having the formula VI,

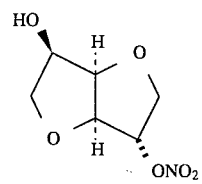

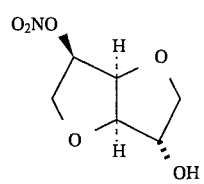

which are both important as therapeutic agents for coronary diseases.

6 Claims, 1 Drawing Sheet

PROCESS FOR THE ENZYMATIC PRODUCTION OF ISOMERICALLY PURE ISOSORBIDE-2 AND 5-MONOESTERS AS WELL AS THEIR CONVERSION INTO ISOSORBIDE-2- AND 5-NITRATE

This application is a divisional of Ser. No. 08/191,731 filed Feb. 4, 1994, now U.S. Pat. No. 5,538,891 which is a continuation-in-part of Ser. No. 07/938,938 filed Sep. 1, 1992 (abandoned).

The invention concerns an enzymatic process for the production of enantiomerically pure and isomerically pure compounds having the general formula I

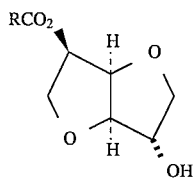

in which R=H and alkyl denotes C1–C17 alkyl which is preferably substituted or halogenated, if desired, as well as isomerically pure compounds having the general formula II

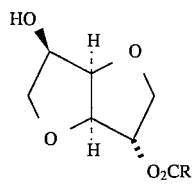

in which R=H and alkyl denotes C1–C17 alkyl which is preferably substituted or halogenated, if desired. In this process isosorbide (1,4:3,6-dianhydro-D-sorbitol) having the formula III

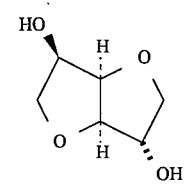

is converted selectively into isomerically pure compounds having the general formula I by regio-selective enzymatic esterification.

Alternatively a diester of isosorbide having the general formula IV

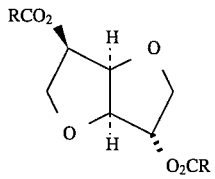

in which R=H and alkyl denotes C1–C17 alkyl which is preferably substituted or halogenated, if desired, is selectively converted into isomerically pure compounds having the general formula II by enzymatic hydrolysis or alcoholysis.

The isomerically pure compounds having the general formulae I and II which are obtained virtually quantitatively in this process are starting materials for the production of the isomerically pure as well as enantiomerically pure pharmaceutical agents isosorbide-2-nitrate of formula V and isosorbide-5-nitrate of formula VI.

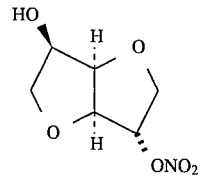

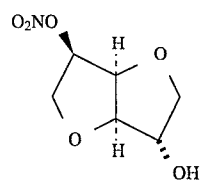

For this compounds having the general formula I are firstly nitrated and afterwards the acyl residue is cleaved off. In this process isosorbide-2-nitrate of formula V is obtained. Starting with compounds having the general formula II one obtains isosorbide-2-nitrate of formula VI in an analogous manner. Both compounds of formulae V and VI are important therapeutic agents for the treatment of coronary diseases such as e.g. angina pectoris.

Organic nitrates e.g. isosorbide-2,5-dinitrate (ISD) have been used for a long time for the therapy of coronary diseases such as e.g. angina pectoris. In studies of the metabolism of these compounds in the organism it was established that isosorbide-2-mononitrate and isosorbide-5-mononitrate have a similar action to ISD (e.g. R. L. Wendt, J. Pharmacol. Exp. Ther. 180, 732 (1971)], whereby the administration of the mononitrates has therapeutic advantages over ISD. A particular distinguishing feature of these compounds is their higher bioavailability and longer half-life.

Up to now an obstacle to the practical application of isosorbide-2-nitrate and isosorbide-5-nitrate has been the complicated and mostly not very selective synthesis of these compounds.

The production of these compounds is described in a series of publications and patents [I. G. Czizmadia, L. D. Hayward, Photochem. Photobiol. 4, 657 (1965); M. Anteunis et al., Org. Magnetic Resonance 3, 363 (1971); D. L. Hayward et al., Can. J. Chem. 45, 2191 (1967); DE 2 751 934; U.S. Pat. No. 4,065,488].

It is not possible with any of these described processes to produce isomerically pure isosorbide-2-nitrate or isosorbide-5-nitrate without complicated separation process such as e.g. chromatography, extraction, recrystallization, derivatization etc.

Such purification steps are always associated with considerable losses in yield which make it impossible to produce these pharmaceutical agents economically.

A more selective method for the production of isosorbide-2-nitrate is described in DOS 2 903 983. In this process isomannide is firstly converted by means of a trifluoromethylmethanesulfonic acid-halide in the presence of an acid trap or with trifluoromethanesulfonic acidanhydride. Reaction of the isomannide-2-trifluoromethanesulfonic acid esters which are preferentially obtained in this way with alkali, earth alkali or organic nitrates yields the desired isosorbide-2-nitrate with inversion of the configuration at the C(2) carbon of the ring system.

A problem in the technical application is the relatively poor yields. Another impediment to a technical application is the relatively expensive reagents and the difficulty in preparing isomannide.

If, however, the aforementioned inversion is firstly carried out with benzoic acid or salts of benzoic acid, afterwards nitrating and cleaving off the ester group then according to DOS 2 903 927 isosorbide-5-nitrate is obtained. Again the expensive isomannide is used.

A further method of preparing isosorbide-2-nitrate starting with isosorbide is described in DE 3 124 410 A1 (cf. also P. Stoss et al., Synthesis 1987, 174]. In this process a regioselective acylation of isosorbide in the 5-position by carboxylic acid anhydride is achieved by the alternative use of metal catalysts such as lead tetraacetate, while the uncatalysed reaction preferably leads to isosorbide-2-ester. The products obtained in this way are subsequently nitrated and the ester group is cleaved off by transesterification to produce isosorbide-2-nitrate or isosorbide-5-nitrate.

A disadvantage of this process has proven to be the use of toxic metal salts in a synthesis of compounds which are to be used therapeutically. The reactions are regioselective but not regiospecific. Also it appears that the control of the reaction conditions in the direction of the desired acylation products is by no means an easy matter.

An enzymatic method has not yet been described for the production of isomerically pure isosorbide-2- or 5-monoesters which are key compounds in the synthesis of isosorbide-5- or 2-nitrate.

In summary it can be ascertained that all previously known processes for the production of isosorbide-2-nitrate and isosorbide-5-nitrate have serious deficiencies in the method or economic disadvantages.

A highly selective method is required for the production of isosorbide-5- and 2-monoesters having the general formulae I and II which can be carried out simply and inexpensively. In addition it should be a process with which—starting from the simply and cheaply available isosorbide—both compounds having the general formulae I and II can be obtained selectively and isomerically pure in high yields and avoiding complicated purification steps. This would also enable the production of the isomerically pure pharmaceutical agents isosorbide-2-nitrate and isosorbide-5-nitrate in a simple and cheap manner.

The present invention describes such a process with which (a) isosorbide-5-monoesters (I) are obtained selectively, isomerically pure and in high yields by enzymatic esterification of isosorbide (III) and isosorbide-2-monoesters (II) are obtained selectively, isomerically pure and in high yields by enzymatic hydrolysis or alcoholysis of isosorbide-2,5-diesters (IV) which can be converted chemically into (b) isosorbide-2-nitrate (V) and isosorbide-5-nitrate (VI).

The invention is described in detail in claims 1–19 and in the following.

In the past years enzymes have increasingly proven to be attractive reagents in organic synthesis because of their highly selective properties. This applies particularly to hydrolases (esterases, lipases, proteases) which have often been used for the production of enantiomerically pure hydroxy compounds by enantioselective hydrolysis or esterification.

Surprisingly it was now found that such ester hydrolases are also eminently suitable for the regioselective differentiation of the 2- and 5-hydroxy groups in the already enantiomerically pure isosorbide (III) and thus allow alternatively the selective production of the isomerically pure isosorbide-5-monoesters (I) or isosorbide-2-monoesters (II).

Isosorbide which is commercially available as well as isosorbide-2,5-diacetate (IV, R=$CH_3$) which can be obtained easily, quantitatively and cheaply from it by acylation with acetic acid anhydride serves as the sole starting material for the reactions described in the following. In principle all isosorbide-2,5-diesters are suitable as starting materials for the hydrolyses and alcoholyses described below. The diacetate is preferably used for reasons of cost as well as because of the low molecular weight of the compounds which are formed from it. In all cases the ester groups are temporary protective groups which have to again be cleaved off for the production of the nitrates.

The enzymatic hydrolysis of isosorbide-2,5-diacetate (IV, R=$CH_3$) [2,5-Di-O-acetyl, 1,4:3,6-dianhydro-D-sorbitol] is carried out in aqueous phosphate buffer at pH 7 in the presence of a hydrolase. During the enzymatic hydrolysis the pH value decreases considerably and is kept constant at pH 7 by the continuous addition of 1 molar sodium hydroxide solution by means of an autotitrator (or alternatively with a peristaltic pump). Since the diacetate used is solid, this two-phase reaction proceeds in the described manner but very slowly. It was found that the addition of small amounts of THF to the reaction medium surprisingly leads to a considerable acceleration of the reaction.

The enzymatic conversion proceeds with an extremely high selectivity, it is solely the acetate group at the C(5)-position which is hydrolyzed. In this way isomerically pure isosorbide-2-acetate (II, R=$CH_3$) is obtained in virtually quantitative yield (>90% isolated) (cf. FIG. 1).

In principle all hydrolases are suitable for carrying out the enzymatic hydrolyses provided they have a high selectivity. Commercially available lipases from Pseudomonas or *Mucor miehei* strains are preferred whereby the commercially available lipases from *Pseudomonas fluorescens* (Amano Pharmaceuticals Co., Boehringer Mannheim) have proven to be particularly suitable.

The amount of enzyme necessary depends on the hydrolytic acitivity of the biocatalyst. The best ratio of substrate and enzyme in each case must be determined empirically under the specific reaction conditions of the experiment. One should endeavour to obtain a space-time yield which is as high as possible.

The reactions are carried out at pH 5–9. pH 6–8 is preferred, pH 7 is especially preferred.

Such reactions are usually carried out in two-phase systems consisting of the solid or liquid substrate as well as an aqueous buffer in a ratio of 1:10 to 10:1. A ratio of 1:10 to 1:2 is particularly preferred.

Such hydrolyses are usually carried out in the presence of buffers in order to facilitate the maintenance of a constant pH value. However, a buffer is not an essential prerequisite for successfully carrying out the process. Enzymatic hydrolyses can also be carried out in aqueous solutions with a low salt content. The pH can also be kept constant by using other bases such as e.g. ammonia.

As described above the addition of cosolvents (e.g. THF, acetone etc.) has proven to be essential for the success of the process.

Such enzymatic hydrolyses are usually carried out at temperatures between 0°–70° C. It is particularly preferable to carry them out at the temperature optimum of the enzyme which is usually 30°–60° C. but well below the temperature maximum of ca. 65° C. The reactions may, however, also be carried out at room temperature. This range is often chosen in the laboratory for reasons of convenience.

In principle all isosorbide-2,5-diesters with fatty acid residues having a chain length of C-1 to C-18 are suitable for carrying out the process. In all cases they are of course the natural substrates of the biocatalysts used. As mentioned above the diacetates were preferably used for practical and economic reasons.

Isosorbide-2-acetate (II, R=CH$_3$) which is formed solely in the selective enzymatic hydrolyses is isolated from the reaction mixture by simple extraction and crystallizes out in pure form after removing the solvent.

As an alternative to the enzymatic hydrolysis the same transformation can also be achieved by enzymatic alcoholysis. In this process the aqueous two-phase system is replaced by a homogeneous organic reaction medium. Instead of water an alcohol is used as the nucleophilic reaction component. For this isosorbide-2,5-diacetate (IV, R=CH$_3$) is dissolved in acetone, an excess of n-heptanol is added and the mixture is stirred until an ester group has been completely cleaved off.

Again it is solely the ester group at C(5) which is cleaved off and in this process isosorbide-2-acetate is obtained virtually quantitatively.

The aforementioned arguments with regard to the enzymes used, the selected reaction conditions and the isosorbide-2,5-diesters used as starting materials apply identically.

In principle all organic solvents are suitable as reaction media provided the hydrolases used still have an adequate activity in them. This must be determined under the specific reaction conditions preferably empirically just in the same way as the optimal ratio of substrate and enzyme.

In principle all alcohols with an adequate nucleophilicity for carrying out such enzymatic alcoholyses are suitable. For practical reasons, in particular in order to isolate and process the products in a simple manner, alcohols are preferably chosen whose esters (e.g. heptyl acetate) can be easily separated by distillation.

As an alternative to the aforementioned hydrolyses and alcoholyses of isosorbide-2,5-diesters, it is also possible to enzymatically esterify isosorbide (III) and this even has the same high selectivity. For this isosorbide is dissolved in acetone and again it is acylated in the presence of hydrolases using vinyl acetate as the acyl donor. The enzymatic esterification again proceeds with an extremely high selectivity and is specific for the 5-position of isosorbide. In this process isosorbide-5-acetate (I, R=CH$_3$) is obtained in a virtually quantitative reaction (cf. FIG. 2).

All organic solvents are in principle suitable as reaction media provided that they cannot themselves be esterified such as e.g. alcohols. Their suitability should preferably be determined empirically under the specific reaction conditions.

All acyl donors (carboxylic acid, carboxylic acid esters, carboxylic acid anhydrides, glycerides, alkenyl esters etc.) are in principle suitable for carrying out such enzymatic esterifications. Vinyl esters are preferred since these allow the enzymatic esterification to be carried out under conditions in which there is an irreversible acyl transfer. The vinyl alcohol released in this process tautomerises spontaneously to form the gaseous acetaldehyde which is thus irreversibly removed from the reaction equilibrium. All vinyl esters having fatty acid chain lengths of C1–C18 are in principle suitable for this. Particularly preferred is vinyl acetate as a cheap acyl donor.

All hydrolases are in principle suitable for carrying out enzymatic esterifications provided they have the required high selectivity. Again commercially available lipases are preferred from the *Pseudomonas fluorescens* strains (Amano Pharmaceutical Co., Boehringer Mannheim). The esterification is also possible with other hydrolases e.g. a lipase from *Mucor miehei*. Again it is found to be highly selective, however, the reaction is very slow, the conversion remains incomplete and thus necessitates a separation process to isolate the products.

As a result of the extremely high selectivities, the complementary formation of both stereoisomers and the simple procedures for the reactions in the described process, all essential requirements are fulfilled for a successful technical application of the method.

Thus both isomers, isosorbide-5-acetate (I, R=CH$_3$) and isosorbide-2-acetate (II, R=CH$_3$) can be obtained selectively without complicated purification steps and virtually quantitatively in an isomerically pure form. They are therefore also available as starting materials for conversion into the corresponding isosorbide-2-nitrate (V) as well as into isosorbide-5-nitrate (VI).

BRIEF DESCRIPTION OF DRAWINGS

For this isosorbide-2-acetate is for example firstly nitrated with nitric acid in glacial acetic acid or acetic acid anhydride and subsequently the acetate group is cleaved off with potassium carbonate in methanol. In this process isosorbide-5-nitrate is obtained in an isomerically pure form and in excellent yield (FIG. 1).

Isosorbide-5-acetate can be converted into isosorbide-2-nitrate in an analogous manner (FIG. 2). The properties of all synthesized products are summarized in Table 1.

Figure 1:
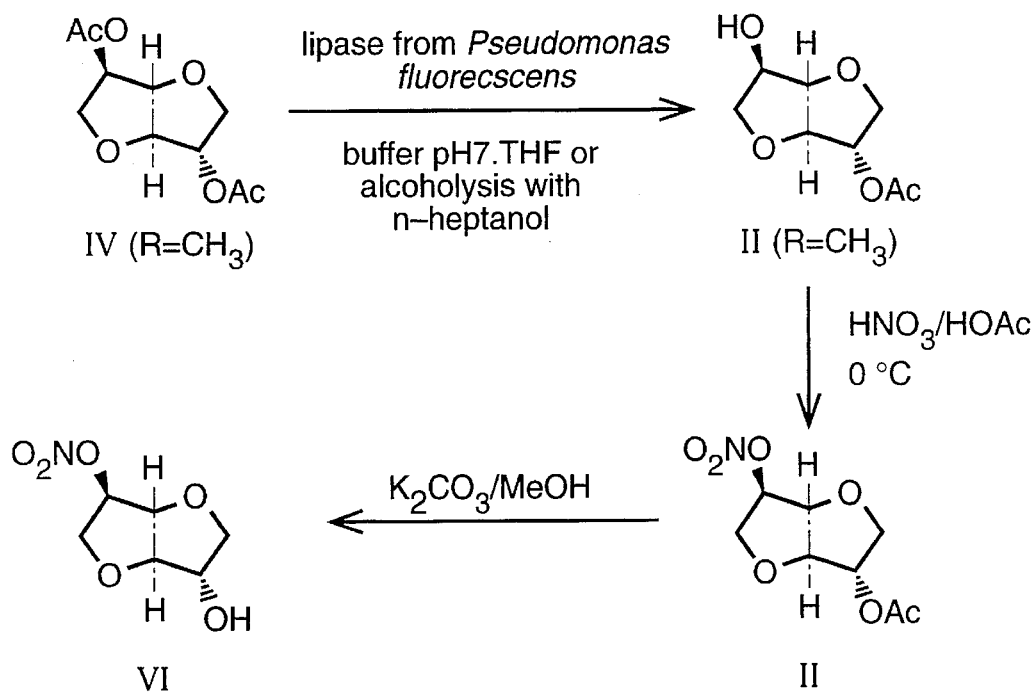
Figure 2:
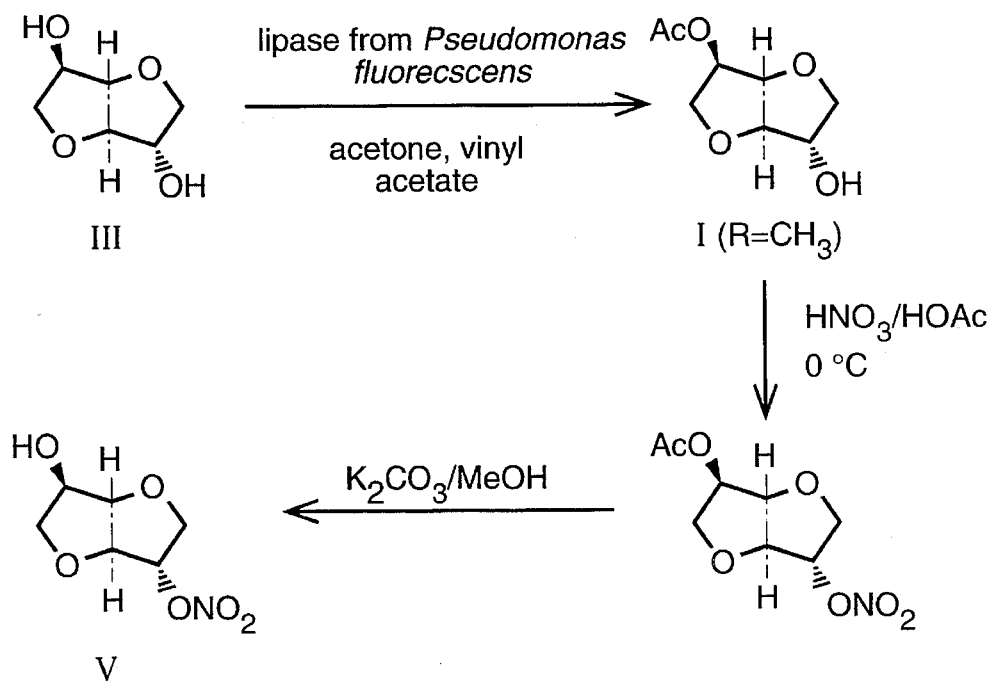

The surprisingly high selectivity of enzymatic reaction steps has led to an extremely simple method for preparing these compounds of pharmaceutical interest which should be readily applicable on a commercial scale.

The invention is elucidated further in the following examples.

Table 1:

Isosorbide-2-acetate: colourless, crystalline substance; m.p. 75°–76° C.;

TLC (diethyl ether): R$_f$=0.28; [α]$_D^{20}$=+77.1° (c=1.12, ethyl acetate).

Isosorbide-5-acetate: colourless, viscous liquid TLC (diethyl ether): R$_f$=0.30; [α]$_D^{20}$=+117.9° (c=1.36, ethyl acetate).

Isosorbide-2-nitrate: colourless, crystalline substance; m.p. 52°–53° C.;

TLC (hexane: diethyl ether 1:1): R$_f$=0.11

Isosorbide-5-nitrate: colourless, crystalline substance; m.p. 88° C.;

TLC (hexane: diethyl ether 1:1): R$_f$=0.10; [α]$_D^{20}$=+181° (c=0.99, ethyl acetate)

2-O-acetyl-isosorbide-5-nitrate: colourless crystalline substance; m.p. 95°–96° C.

TLC (hexane: diethyl ether 1:1): R$_f$=0.36; [α]$_D^{20}$=+163° (c=1.00; ethyl acetate)

5-O-acetyl-isosorbide-2-nitrate: colourless, highly viscous liquid

TLC (hexane: diethyl ether 1:1): R$_f$=0.38

Isosorbide-2-acetate
[1,4:3,6-dianhydro-D-sorbitol-2-acetate]

EXAMPLE 1

2.64 g (11.5 mmol) isosorbide-2,5-diacetate is suspended in 20 ml phosphate buffer, pH 7.0 and 200 mg lipase from *Pseudomonas fluorescens* (SAM II, Amano Pharmaceuticals) is added. The pH value is kept constant by addition of 1 molar sodium hydroxide solution using an autoburette. After 10.95 ml 1M sodium hydroxide solution (40 hours) have been consumed, the preparation is extracted continuously for 24 hours with ethyl acetate. The organic phase is dried over $MgSO_4$ and the solvent is removed. The crude product is separated by column chromatography (silica gel 60) in diethyl ether.

Yield: 494 mg (3.38 mmol) isosorbide (29%) colourless crystalline substance m.p. 61°–62° C.

180 mg (0.96 mmol) isosorbide-2-acetate (8%) colourless crystalline substance m.p. 70°–71° C.

1070 mg (4.65 mmol) isosorbide-2,5-diacetate (40%) colourless highly viscous liquid

EXAMPLE 2

2.30 g (10 mmol) isosorbide-2,5-diacetate is dissolved in 5 ml absolute THF and 20 ml phosphate buffer, pH 7.0 and 400 mg lipase from *Pseudomonas fluorescens* (SAM II, Amano Pharmaceuticals) are added, and after 10.03 ml 1M sodium hydroxide solution (48 hours) have been consumed it is processed according to Example 1.

Yield: 1.60 g (8.50 mmol) isosorbide-2-acetate (85%) colourless crystalline substance m.p. 72°–73° C.

EXAMPLE 3

6.91 g (30 mmol) isosorbide-2,5-diacetate is dissolved in 15 ml absolute THF, 60 ml phosphate buffer, pH 7.0 and 500 mg lipase from *Pseudomonas fluorescens* (SAM II, Amano Pharmaceuticals) are added, and after 29.07 ml 1M sodium hydroxide solution (24 hours) have been consumed it is processed according to Example 1.

Yield: 5.00 g (26.7 mmol) isosorbide-2-acetate (89%) colourless crystalline substance m.p. 75°–76° C.

EXAMPLE 4

2.30 g (10 mmol) isosorbide-2,5-diacetate is dissolved in 15 ml acetone, 5 ml n-heptanol 200 mg lipase from *Pseudomonas fluorescens* (SAM II, Amano Pharmaceuticals) is added, and it is stirred at room temperature. After 12 days the enzyme is removed by filtration, it is washed thoroughly with acetone and the solvent as well as the excess of n-heptanol and the heptyl acetate which formed are removed by distillation.

Yield: 1.71 g (9.09 mmol) isosorbide-2-acetate (91%) colourless crystalline substance m.p. 75°–76° C.

Isosorbide-5-acetate
[1,4:3,6-dianhydro-D-sorbitol-5-acetate]

EXAMPLE 5

1.46 g (10 mmol) isosorbide is dissolved in 20 ml acetone, 2.77 ml (30 mmol) vinyl acetate and 200 mg lipase from *Pseudomonas fluorescens* (SAM II, Amano Pharmaceuticals) is added, and it is stirred at room temperature. After 3 days the enzyme is removed by filtration, it is washed thoroughly with acetone and the solvent is removed. The crude product is distilled on a bulb tube.

Yield: 1.70 g (9.03 mmol) isosorbide-5-acetate (90%) colourless viscous liquid b.p. 125° C./0.08 mbar

EXAMPLE 6

14.61 g (100 mmol) isosorbide is dissolved in 150 ml acetone, 22 ml (300 mmol) vinyl acetate and 500 mg lipase SAM II are added, and it is stirred for 6 days at room temperature. Subsequently the enzyme is removed by filtration, it is washed with acetone, the solvent is removed and the crude product is distilled in a high vacuum.

Yield: 16.90 g (89.9 mmol) isosorbide-5-acetate (90%) colourless viscous liquid b.p. 130° C./0.09 mbar Isosorbide-2-nitrate
[1,4:3,6-dianhydro-D-sorbitol-2-nitrate]

EXAMPLE 7

0.2 ml 65% nitric acid is mixed at 0° C. with 0.8 ml acetic acid anhydride, and a solution of 0.2 ml dichloromethane and 330 mg (1.75 mmol) isosorbide-5-acetate is added dropwise at this temperature. It is stirred for a further 20 minutes at room temperature, 0.4 ml dichloromethane and 1 ml water are added and the phases are separated. The organic phase is extracted with dilute ammonia solution until it is neutral, it is dried over $MgSO_4$ and the solvent is removed.

Yield: 400 mg (1.7 mmol ) 5-O-acetyl-isosorbide-2-nitrate (98%) colourless, highly viscous liquid 400 mg (1.7 mmol) 5-O-acetyl-isosorbide-2-nitrate is added to 10 ml methanol and 50 mg potassium carbonate and the mixture is stirred for 12 hours at room temperature. Subsequently the solvent is removed, the residue is taken up in 2 ml water and extracted four times with 10 ml ethyl acetate each time. The solvent is removed from the combined organic phase and the residue is dried in a high vacuum.

Yield: 300 mg (1.56 mmol) isosorbide-2-nitrate (89%) colourless crystalline substance m.p. 52°–53° C.

Isosorbide-5-nitrate
[1,4:3,6-dianhydro-D-sorbitol-5-nitrate]

EXAMPLE 8

1.4 ml 65% nitric acid is mixed at 0° C. with 5.5 ml acetic acid anhydride, and a solution of 1.4 ml dichloromethane and 2.6 g (13.8 mmol) isosorbide-2-acetate is added dropwise at this temperature. It is stirred for a further 20 minutes at room temperature, 2.8 ml dichloromethane and 6.9 ml water are added and the phases are separated. The organic phase is extracted with dilute ammonia solution until it is neutral, it is dried over $MgSO_4$ and the solvent is removed.

Yield: 2.73 g (11.7 mmol) 2-O-acetyl-isosorbide-5-nitrate (85%) colourless crystalline substance m.p. 95°–96° C.

800 mg (3.4 mmol) 2-O-acetyl-isosorbide-5-nitrate is added to 20 ml methanol and 100 mg potassium carbonate and the mixture is stirred for 14 hours at room temperature.

Subsequently the solvent is removed, the residue is taken up in 20 ml water and extracted 6 times with 20 ml ethyl acetate each time. The solvent is removed from the combined organic phase and the residue is dried in a high vacuum.

Yield: 590 mg (3.1 mmol) isosorbide-5-nitrate (91%) colourless crystalline substance m.p. 88° C.

We claim:

1. A isometrically pure process for producing an isosorbide -5-nitrate of formula

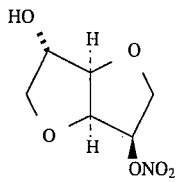

comprising: reacting an isosorbide-2-ester of formula

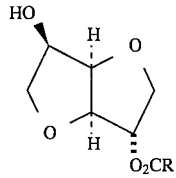

with a nitrate to form a second ester, hydrolyzing said second ester to form isometrically pure isosorbide-5-nitrate, and recovering said isometrically pure isosorbide-5-nitrate.

2. The process of claim 1, wherein R is C1–C17 alkyl substituted by a halogen.

3. The process of claim 1, wherein said isosorbide-2-ester is isosorbide-2-acetate.

4. A process for producing an isometrically pure, isosorbide-2-nitrate of formula:

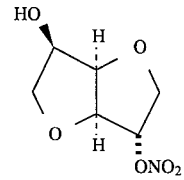

comprising reacting an isosorbide-5-ester of formula:

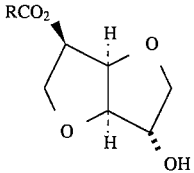

wherein R is H, C1–C17 alkyl or substituted C1–C17 alkyl with a nitrate to form a second ester, hydrolyzing said second ester to form said isometrically pure isosorbide-5-ester, and recovering said isometrically pure isosorbide-5-ester.

5. The process of claim 4, wherein said isosorbide-2-ester is isosorbide-2-acetate.

6. The process of claim 4, wherein R is C1–C17 alkyl, substituted with halogen.

* * * * *